United States Patent [19]

Gregory et al.

[11] 3,951,852

[45] Apr. 20, 1976

[54] PROCESS FOR THE PREPARATION OF ALUMINA GEL

[75] Inventors: George Keith Emerson Gregory, Marlow; James Marchant Peach, High Wycombe; James Campbell Newell, Bushey, all of England

[73] Assignee: John Wyeth & Brother Limited, Taplow, England

[22] Filed: Feb. 19, 1974

[21] Appl. No.: 443,651

Related U.S. Application Data

[63] Continuation-in-part of Ser. No. 239,604, March 30, 1972, abandoned, which is a continuation-in-part of Ser. No. 847,974, Aug. 6, 1969, abandoned.

[30] Foreign Application Priority Data

Aug. 16, 1968 United Kingdom............... 39202/68

[52] U.S. Cl............................... 252/317; 424/127; 424/154; 424/156
[51] Int. Cl.² ................... B01J 13/00; A61K 13/06; A61K 13/10
[58] Field of Search ............ 252/317; 424/127, 154, 424/156; 423/628, 629, 630

[56] References Cited

UNITED STATES PATENTS

| 2,137,638 | 11/1938 | Sondern et al...................... 424/157 |
| 2,166,868 | 7/1939 | Jones.................................. 424/157 |
| 3,239,416 | 3/1966 | Rubino .............................. 424/157 |
| 3,395,221 | 7/1968 | Snyder et al........................ 424/157 |

FOREIGN PATENTS OR APPLICATIONS

| 202,756 | 4/1955 | Australia............................. 424/156 |
| 423,541 | 12/1933 | United Kingdom................ 424/157 |

*Primary Examiner*—Benjamin R. Padgett
*Assistant Examiner*—Christine M. Nucker

[57] ABSTRACT

The invention provides a process for the preparation of alumina gels possessing a high alumina content, namely from 10% to 16%. The gels are useful in the production of antacid preparations. The gels are prepared by admixing a solid aluminium sulphate with an aqueous solution of a carbonate and bicarbonate, thickening the precipitated gel, washing and thickening the gel again.

3 Claims, No Drawings

PROCESS FOR THE PREPARATION OF ALUMINA GEL

This invention is a continuation-in-part of our application Ser. No. 239,604 filed Mar. 30, 1972, now abandoned, which itself is a continuation-in-part of application Ser. No. 847,974, filed August 6, 1969, both of which are now abandoned.

The invention relates to an improved process for the preparation of alumina gel for the preparation of antacid formulations or for the preparation of alumina for pharmaceutical or general use.

Alumina gel is a well-known constituent in many antacid preparations on the market. At the present time, the gel usually is made by batch-wise addition of a solution of an aluminium salt (e.g., aluminium chloride or aluminium sulphate) to a solution of a soluble carbonate or bicarbonate (e.g., sodium carbonate or sodium bicarbonate) in large vats. The precipated gel so formed generally contains about 1% by weight of alumina and usually is concentrated to about half volume, usually by filtration (including straining and centrifuging) before being washed on a filter to remove excess alkali as well as the ions of the aluminium salt used. The washing generally is carried out at constant volume by running in water at the same rate as filtrate is removed. When the analysis of the gel formed is within that desired the gel is strained until the solids content is high enough for compounding. In the compounding step excipients are added and the final mixing carried out. If the gel is then to be used for the preparation of a powder it is transferred to a standard drying apparatus for further treatment.

Furthermore, it has recently been reported (see Gastroenterology Vol. 52 No. 6 page 1009; Gut Vol. 6 pages 506–508 and Gut Vol. 5 pages 581–585) that alumina antacid dosage levels used in products marketed at the present time probably are too low to achieve complete and prolonged acid neutralization. There is clearly a desire for an alumina gel which can be prepared in an increased strength compared with the prior art material while maintaining its pourable quality.

We have now found a new and simple process which provides an improved alumina gel. The process results in novel alumina gels characterized by a high alumina content. In particular, the gels have an alumina content of 10% to 16%. The novel gels possess advantages in that they can be more efficiently spray-dried to form powders and more conveniently transported as the gel in comparison to gels of lower alumina content.

The invention provides a process for the preparation of an alumina gel, which comprises:
a. admixing a solid aluminium sulphate with an aqueous solution of a mixture of an alkali metal carbonate and an alkali metal bicarbonate to precipitate an alumina gel,
b. straining or thickening the gel,
c. washing the gel and
d. thickening the washed gel until the resultant gel has an alumina content within the range of from 10% to 16%.

It is surprising that the process results in gels of such a high alumina content since the alumina gels of the prior art have lower alumina contents. In particular, the prior art methods mentioned above normally yield alumina gels of up to 6% alumina.

In the first step of the process of the invention, a solid aluminium sulphate is admixed with an aqueous solution of a mixture of an alkali metal carbonate and an alkali metal bicarbonate. As the solid aluminium sulphate, we prefer to use aluminium sulphate hexadecahydrate. The relative proportions of the alkali metal carbonate and alkali metal bicarbonate are not critical and the ratio by weight of carbonate to bicarbonate may range from 6:1 to 1:6, particularly 2:1 to 1:2. The alkali metal carbonate and bicarbonate are preferably sodium carbonate and sodium bicarbonate, respectively, but potassium carbonate and/or potassium bicarbonate may be used instead. It has been found convenient to use a crude commercial mixture of sodium carbonate and sodium bicarbonate in the ratio of about 1.25:1 by weight respectively and which is known as 'Crex' (Trade Mark). Such a mixture has the particular advantage of cheapness.

The relative proportions of the aluminium sulphate and the mixture of alkali metal carbonate and alkali metal bicarbonate are critical in that a very high degree of neutralization of the base results in gels of high viscosity, whilst low degrees of neutralization of the base can be wasteful. We recommend that the solid aluminium sulphate is added in an amount such that the percentage neutralization of the aqueous solution of base is from 65% to 90%, preferably 80% to 85%. The concentration of the mixture of alkali metal carbonate and alkali metal bicarbonate in the aqueous solution should be at least about 85 grams per liter. It may range from about 85 grams per liter up to saturation, preferably 110 grams per liter to 200 grams per liter. It is normally found that high concentrations of the base favour high alumina content and therefore it is recommended to avoid using concentrations below 85 grams per liter.

The reaction temperature for the interaction of the aluminium sulphate with the base may lie within the range of 10°C to 35°C, preferably 15°C to 30°C. In particular, one may use room temperature, i.e. 10° to 20° or 25°C. During the course of the addition of the solid aluminium sulphate to the aqueous solution to form the gel and after the gel is formed, it is recommended to agitate the mixture thoroughly, for example, by stirring. The period of time over which the solid aluminium sulphate is added is not critical, but it is believed that long time/high temperature combinations should be avoided as causing an increase in viscosity and making the washing process difficult.

The addition of the solid aluminium sulphate to the reaction mixture causes the alumina gel to precipitate. After the gel has formed it is strained or thickened to a convenient volume for washing. This first dewatering step is suitably effected by using a straining bag. After the gel has been thickened, it is washed to remove undesired ions. It is preferred to subject the gel to agitation during washing. After the washing step, the gel is subjected to a second dewatering stage. This can be effected by filtration, for example, using a filter press. It has been surprisingly found that thickening of the gel can be carried out to remove a substantial proportion of water so that the resultant gel has an alumina content of from 10% to 16%. When the gel is recovered from the filter, it may take the appearance of a solid filter cake, but on subjecting the cake to agitation, a fluid gel is obtained. Frequently, the gel may be sufficiently fluid to be pumped to a spray-drier for powder formation, especially if the alumina content is up to about 12%, but if the gel proves too viscous, a small dilution with water enhances the flow properties.

If desired the alumina gel obtained in accordance with the new process may be processed by spray-drying. The alumina gel is particularly advantageous for spray-drying in comparison with known gels because less water has to be removed to obtain a powder. If desired the gel may be combined with conventional additives prior to spray-drying.

The alumina gel obtained in accordance with the present invention may also be used in antacid gels. They may be used in similar manner to conventional alumina gels of lower alumina content, for example, up to 6% alumina. However, the new gels possess an advantage over such conventional gels in that they can be transported to the location of use more cheaply as a result of the lower water content to be carried. The new alumina gels are particularly useful for compounding with other ingredients to form antacid gels. Prior to compounding they may be thinned to lower concentration by adding water. As standard materials with which the new gels may be compounded, there may be mentioned magnesium oxide, silicones, preservatives (e.g. methyl and propyl hydroxybenzoates) and flavourings. The hydrated alumina powder produced from the gels of the invention can be used in solid antacid formulations and for general use, for instance, as a catalyst support, as a drying agent or for chromatography, after further drying as known to those skilled in the latter arts. The gels could also be dried directly for such purposes.

EXAMPLE 1

An alumina gel was precipitated over a period of 10 minutes by the addition of 4,389 gms. of solid aluminium sulphate $Al_2(SO_4)_3.16H_2O$ to a solution of 3,832.5 gms of 'Crex' (mixed sodium carbonate and sodium bicarbonate) in 42 liters of water (80% neutralization). Mean figures for assay of 'Crex' are as follows:

| Total alkalinity | $Na_2O$ | 42.66% |
|---|---|---|
| Sodium carbonate | $Na_2CO_3$ | 48.14% |
| Sodium bicarbonate | $NaHCO_3$ | 39.32% |
| Water | $H_2O$ | 12.1% |

The gel was then stirred for 20 minutes before thickened to half volume in a filter bag. The bag was washed at this volume for 14 hours using an amount of wash water equivalent to 4 times the volume of gel and then thickened by straining or filtration to 10.6% (by weight) alumina. Part of the gel was formulated with magnesia paste (containing 20% by weight of magnesia), silicone emulsion, preservatives and flavouring as follows to give a final product containing 7.6% by weight of alumina and 2.6% by weight of magnesia of the following formulation:

| | |
|---|---|
| Alumina gel (10.6% by wt alumina) | 791 gms(to give 7.6% by wt. in final product) |
| Magnesia magma (20% by wt. magnesia) | 14.7 gms (to give 2.6% by wt. in final product) |
| Silicone emulsion 30% by wt. (Midland Silicone M.30) | 16.5 gms |
| 'Nipagin M' (methyl p-hydroxybenzoate) | 2.04 gms |
| Saccharin Sodium B.P. | 0.22 gms |
| 'Nipasol M' (propyl p-hydroxybenzoate) | 0.224 gms |
| Sodium Cyclamate B.P. | 2.2 gms |
| Lemon Mint Flavour (IFF V6409) | 2.475 gms |
| Water | 1100 gms |

The flow time of this gel in a cup viscometer was 22 secs for 100 grams.

EXAMPLE 2

627 grams of solid aluminium sulphate (hexadecahydrate) were added to a solution of 'Crex' (mixed sodium carbonate/bicarbonate) dissolved in 6,000 gms of water at 25°–27°C (80% neutralisation). The precipitate formed was stirred for 20 minutes, strained to half volume and washed in a filter bag with four times the volume of wash water over five hours. The gel was then strained for a further 11 hours after which the content of alumina was 12.2% by weight. This gel was still mobile and was easily spray dried in a Niro Minor Atomiser to give a powder in contrast to gel produced by the prior art method in which the upper limit for spray drying is 6% $Al_2O_3$.

In the drying process, the drying conditions were: inlet temperature 70°–100°C. This Example showed that alumina gels of 12.2% by weight can be fed satisfactorily through the drier.

EXAMPLE 3

This example describes the spray drying of alumina gel prepared in accordance with the invention using a Niro Production Minor spray drier of nominal evaporative capacity 10–25 Kg/hour in comparison with gels thickened to a lower alumina content. Direct gas heating was used and the maximum atomiser speed 28,000 r.p.m. was employed. An inlet temperature of 250°C was used together with an outlet temperature of 85° to 100°C depending on the rate of alumina gel feed. The data obtained is indicated in Table III.

TABLE III

| % $Al_2O_3$ gel. | Outlet Temp °C. | Rate of powder production Kg/hr. | % $Al_2O_3$ in Powder | Antacid Activity Armstrong Martin Powder = 375mg $Al_2O_3$ | Rate of Evaporation Kg/hr. |
|---|---|---|---|---|---|
| 1) 10.11 | 85 | 7.3 | 39.9 | 45/3.8 | 22.5 |
| 2) 10.2 | 95 | 4.2 | 51.8 | 42/3.65 | 17.1 |
| 3) 6.28 | 100 | 2.4 | 52.9 | 40½/3.8 | 17.6 |
| 4) 6.28 | 100 | 1.8 | 53.25 | 42½/3.9 | 13.3 |

Antacid activities
First figure = the time, in minutes, above pH3.0
Second figure = the maximum pH reached.

All samples had good antacid activity on the Armstrong-Martin test.

This Example illustrates that the high alumina gels of the invention have the advantage of being more efficiently processed to a powder than gels of lower alumina content.

EXAMPLE 4

The general procedure of Example 1 was again followed and 2,740 g. 'Crex' in 30.1 of water and 3,140 g. of aluminium sulphate was admixed. The degree of neutralization was 80% giving 14% alumina in precipitate, which was strained, washed, filtered and concentrated to a thin paste containing 13.6% alumina. Sufficient water was added to produce a pourable gel with a viscosity of 1,280 cps. at a shear rate of 20 sec $^{-1}$.

EXAMPLE 5

The procedure of Example 1 was again followed. 1,370 g. 'Crex' in 9.5 l. of water and 1,570 g. aluminium sulphate was admixed, washed, strained and thickened. Upon very slight dilution a thin paste containing 15% alumina was obtained. This was a highly thixotropic suspension and was just pourable upon slight agitation but has a viscosity of 1,130 cp at 20 sec $^{-1}$.

EXAMPLE 6

3,762 Grams of solid aluminium sulphate hexadecahydrate were added to a solution of 3,285 grams of 'Crex' dissolved in 21.6 liters of water (80% neutralization) over a period of 15 minutes at 15.5°C to precipitate an alumina gel. The precipitated gel formed was stirred for one hour and thickened to approximately 12 liters over 40 minutes using a paddle stirrer. The batch was then washed over 40 hours with 7.5 times its volume of wash water and then thickened by means of a straining bag for 8 hours. The gel was then thickened to a concentration of 15.1% $Al_2O_3$ by filtration using a Bruckner filter. 100 grams of the alumina gel were mixed with 53.2 grams of a magnesium oxide magma of 10% concentration and 44.8 grams of water to prepare an antacid gel formulation of good viscosity characteristics.

EXAMPLE 7

7,730 kilograms of aluminium sulphate were added to a solution of 7.620 kilograms of 'Crex' in 40 liters of water at 20.3°C (70% neutralization) and the slurry was stirred for 20 minutes using a Silverson mixer. 33 liters of the product was transferred to a straining bag and thickened to 23 liters. The gel was then washed with 5 times its volume of water in the bag over 27 hours. The mixer was continuously used to stir the gel in the bag before and during washing. The gel was then thickened to a solid cake using a filter press and subsequently liquified by using the mixer for 30 minutes. The alumina content of the gel was 11.3%.

EXAMPLE 8

6.930 kilograms of aluminium sulphate were added to a solution of 6 kilograms of 'Crex' in 31.5 liters of water at 19°C (80% neutralization) with agitation using a Silverson mixer. 18.8 liters were transferred to the bag, thickened to 13.5 liters and the procedure described in Example 7 followed except that the washing proceeded for 21½ hours and the wash water amounted to 9 times the volume of the gel. The alumina content of the product was 11.5%.

EXAMPLE 9

8.820 kilograms of aluminium sulphate were admixed with a solution of 7.620 kilograms of 'Crex' in 40 liters of water (80% neutralization) at 18°C over 30 minutes with agitation by means of a paddle stirrer. The slurry was stirred for another 20 minutes and 30 liters were transferred to a straining bag and the volume reduced to 21 liters. The gel was washed over 24 hours with 4 times its volume of water and the paddle stirrer was used to agitate the gel during this period. After washing, half of the gel was left overnight under high shear agitation provided by a Silverson mixer and thickened with a filter press. The solid filter cake obtained was dispersed by the Silverson mixer to form a homogeneous gel of 11.4% of alumina content.

EXAMPLE 10

8.820 kilograms of aluminium sulphate were added to a solution of 7.620 kilograms of 'Crex' in 40 liters of water (80% neutralization) at 17.5°C with stirring by means of a paddle stirrer with a square paddle at 100 r.p.m. After a precipitation time of 30 minutes the temperature was 14.5°C. 33.5 liters were transferred to a 24 liter capacity bag and washed at that volume for 24 hours with 120 liters of water and agitation by means of the Silverson mixer. After washing, the gel was allowed to thicken in the bag and then thickened with a filter press to a thick gel as filter cake. The filter cake was thinned by means of the Silverson mixer. Alumina content: 12.1%.

EXAMPLE 11

A gel of 11.3% alumina content was prepared by the procedure of Example 10 with the following modifications. During precipitation and for 17½ hours thereafter the product was stirred with the Silverson mixer. During washing, the product was stirred with the paddle stirrer and the volume of wash water was 108 liters over 27½ hours.

EXAMPLE 12

A gel of 11.9% alumina content was prepared by the procedure of Example 10, with the modification that, during washing, the product was stirred by the paddle stirrer and circulation of the product through the pump of the filter press.

EXAMPLE 13

A gel of 10.8% alumina content was prepared by the procedure of Example 12 with the modification that 6.45 kilograms of 'Crex' and 7.47 kilograms of aluminium sulphate (85% neutralization) were used.

EXAMPLE 14

31 liters of gel were prepared by adding aluminium sulphate to a 19% w/w aqueous solution of 'Crex' (80% neutralization) and 18.8 liters of the product were transferred to a bag and thickened by straining to 13.5 liters. The product was washed for 17 hours at this volume using 6 volumes of water (81 liters) and strained further to approximately 9 liters. At this stage, the alumina content was about 6.85%. The gel was thickened with a roto-vacuum filter and the alumina content was found to be 12.5%. During precipitation and washing, the Silverson mixer was used to provide agitation.

We claim:
1. A process for the preparation of a pourable alumina gel, which comprises
   a. introducing solid aluminium sulphate into an aqueous solution of at least 85 grams per liter of a mixture of sodium carbonate and sodium bicarbonate, said sodium carbonate and sodium bicarbonate being present in a weight ratio of from 1:2 to 2:1, under conditions of good mixing, at a temperature within the range of 10°C. to 35°C. to precipitate an alumina gel, the percentage neutralization of the said mixture of sodium carbonate and sodium bicarbonate by the aluminium sulphate being within the range of 65% to 90%, b. straining or thickening the gel,
c. washing the gel, and
d. thickening the washed gel until the resultant gel has an alumina content within the range of from 10% to 16%.

2. A process as defined in claim 1, wherein the percentage neutralization of the mixture of sodium carbonate and sodium bicarbonate is within the range of about 80% to 85%.

3. A process as defined in claim 1 wherein the aqueous solution contains 110 to 200 grams per liter of the mixture of sodium carbonate and sodium bicarbonate.

* * * * *